US011813001B2

(12) United States Patent
Mari et al.

(10) Patent No.: US 11,813,001 B2
(45) Date of Patent: *Nov. 14, 2023

(54) METHOD AND APPARATUS FOR PERFORMING MEDIAL-TO-LATERAL SACROILIAC FUSION

(71) Applicant: GLOBUS MEDICAL, INC., Audubon, PA (US)

(72) Inventors: Liana Mari, Wynnewood, PA (US); Ryan Kretzer, Tucson, AZ (US)

(73) Assignee: Laurent Sebastien, Sauveterre, PA (US)

( * ) Notice: Subject to any disclaimer, the term of this patent is extended or adjusted under 35 U.S.C. 154(b) by 347 days.

This patent is subject to a terminal disclaimer.

(21) Appl. No.: 17/164,858

(22) Filed: Feb. 2, 2021

(65) Prior Publication Data
US 2021/0153912 A1   May 27, 2021

Related U.S. Application Data

(63) Continuation of application No. 15/907,397, filed on Feb. 28, 2018, now Pat. No. 10,905,472.

(51) Int. Cl.
*A61B 17/70* (2006.01)
*A61B 17/88* (2006.01)
*A61B 17/17* (2006.01)

(52) U.S. Cl.
CPC ...... *A61B 17/7055* (2013.01); *A61B 17/1757* (2013.01); *A61B 17/7076* (2013.01); *A61B 17/7094* (2013.01); *A61B 17/8897* (2013.01)

(58) Field of Classification Search
CPC ............ A61B 17/7055; A61B 17/8897; A61B 17/7094; A61B 17/7076
USPC .................................................. 606/246–279
See application file for complete search history.

(56) References Cited

U.S. PATENT DOCUMENTS 10,905,472 B2 *   2/2021   Mari ................. A61B 17/8625

\* cited by examiner

*Primary Examiner* — Eduardo C Robert
*Assistant Examiner* — Tara Rose E Carter

(57) ABSTRACT

Method and apparatus for performing medial-to-lateral sacroiliac fusion. An aiming guide is used to place a guide wire into a sacroiliac joint to facilitate driving a fusion implant into the joint.

20 Claims, 5 Drawing Sheets

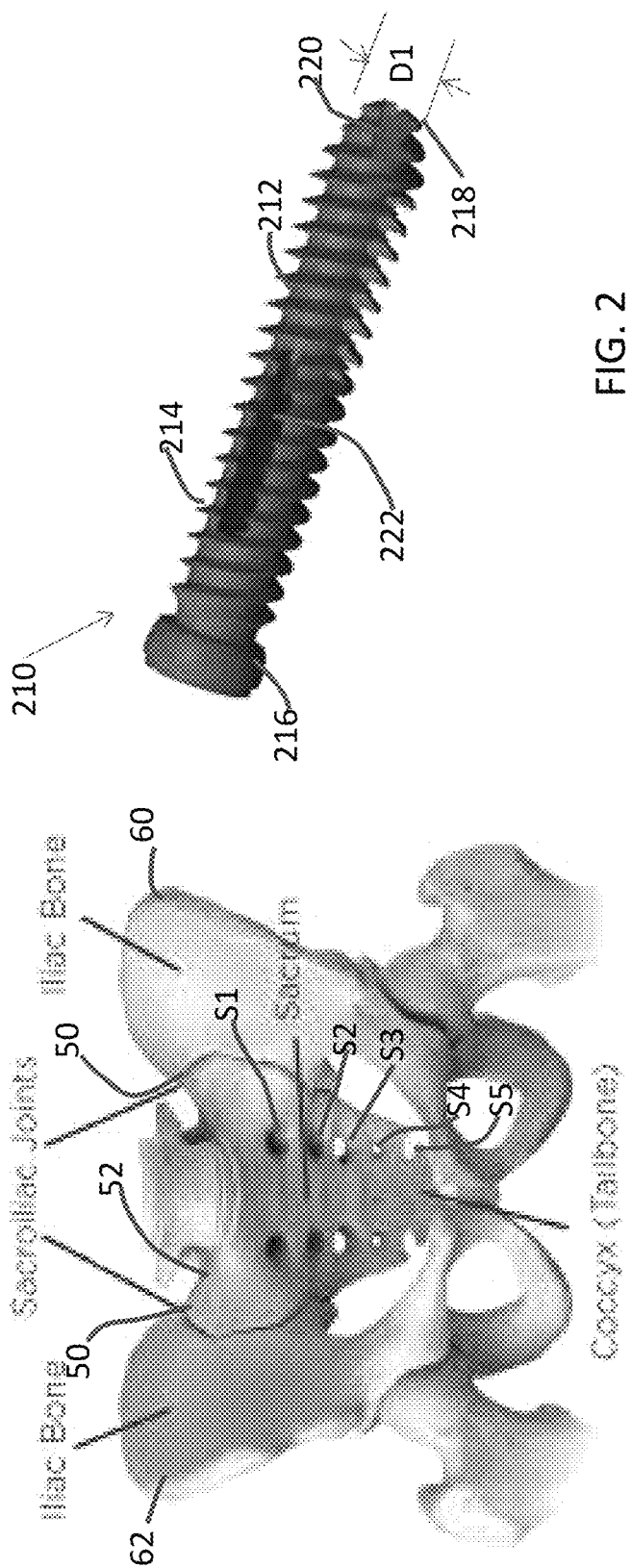

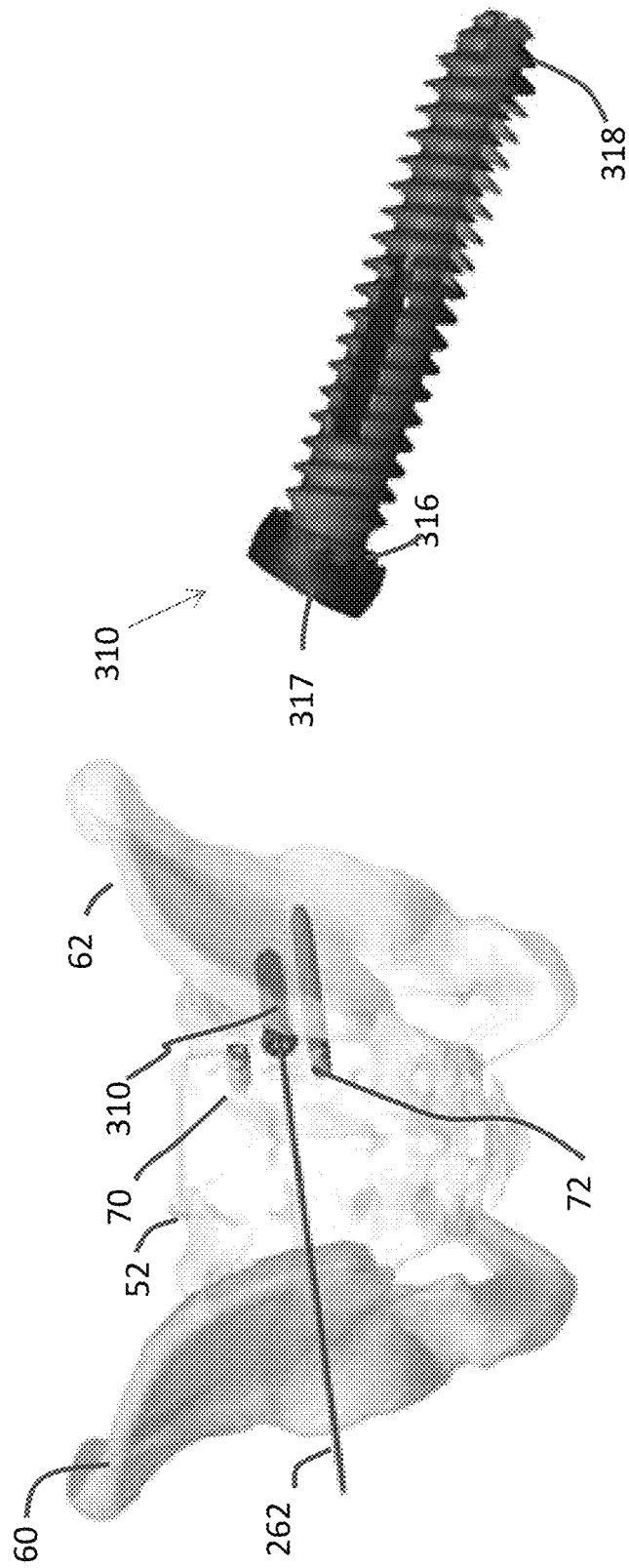

METHOD AND APPARATUS FOR PERFORMING MEDIAL-TO-LATERAL SACROILIAC FUSION

CROSS-REFERENCE TO RELATED APPLICATION

The present application is a Continuation of U.S. patent application Ser. No. 15/907,397, filed on Feb. 28, 2018, which is incorporated herein by reference in its entirety.

BACKGROUND

Field

The present device relates to a method and apparatus for performing a medial-to-lateral sacroiliac fusion.

Description of the Related Art

Currently, no streamlined technique exists to fuse a sacroiliac joint ("SIJ") while implanting posterior pedicle screws. Improper implantation can sometimes lead to loosening of the screws, resulting in poor fusion. Additionally, drawbacks exist for a lateral-to-medial approach, namely, that the SIJ cannot undergo a proper decortication to promote fusion of the sacrum and iliac bones.

Accordingly, there exists a need for a medial-to-lateral sacroiliac fusion approach.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a method for performing a medial-to-lateral sacroiliac fusion can include the steps of inserting a first cannulated screw into the sacrum; inserting a first guide wire into the first cannulated screw; inserting a first leg of an aiming guide through the first guide wire; inserting a second guide wire through a second leg of the aiming guide and into bone; while maintaining the position of the second guide wire, removing the aiming guide; measuring a depth of the second guide wire in the bone; drilling and tapping the bone; and inserting the fusion implant over the second guide wire and into the sacroiliac joint.

In another embodiment, the aiming guide for performing the fusion is provided.

BRIEF DESCRIPTION OF THE DRAWINGS

Other aspects, features, and advantages of the present device will become more fully apparent from the following detailed description, the appended claims, and the accompanying drawings in which like reference numerals identify similar or identical elements.

FIG. 1 is an anterior view of a sacroiliac joint;

FIG. 2 is a perspective view of a fusion implant according to an exemplary embodiment;

FIG. 3 is a perspective view of a fusion implant according to an alternative exemplary embodiment;

FIG. 7 is a posterior view of the implant of FIG. 3 having been implanted into the sacroiliac joint;

DETAILED DESCRIPTION

Figure 5:
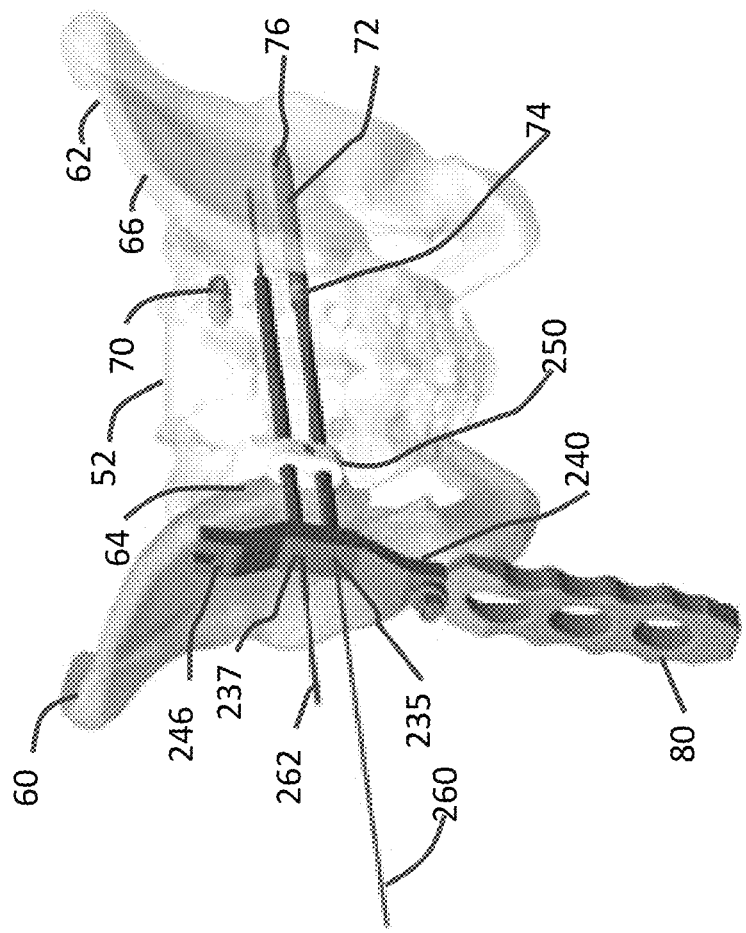
FIG. 5 is a posterior view of the aiming guide of FIG. 4 being used to insert a guide wire for the implant of FIG. 2.

In the drawings, like numerals indicate like elements throughout. Certain terminology is used herein for convenience only and is not to be taken as a limitation on the present device. The terminology includes the words specifically mentioned, derivatives thereof and words of similar import. The embodiments illustrated below are not intended to be exhaustive or to limit the device to the precise form disclosed. These embodiments are chosen and described to best explain the principle of the device and its application and practical use and to enable others skilled in the art to best utilize the device.

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present device.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides a medial to lateral posterior sacroiliac joint (SIJ) fusion technique. The medial to lateral posterior sacroiliac joint (SIJ) fusion may be performed by means of an aiming guide. The technique may address the need for SIJ fusion while implanting posterior instrumentation. Starting from midline, a fusion implant is placed across the SIJ in a medial to lateral S2 alar iliac (S2AI) trajectory. The trajectory of the fusion implant is parallel to or within 10 degrees of an S2AI screw trajectory. The S2AI screw trajectory is from the S2 sacrum into the ilium while crossing the SIJ. The fusion implant may be above or below the S2AI screw and one or more fusion implants may be placed across the SIJ.

Referring to FIG. 1, the anatomy of a typical sacroiliac joint 50 ("joint 50") and associated structure is shown. A sacrum 52 is disposed between a left ilium 60 and a right ilium 62 and includes S1-S5 sacral foramina. The joint 50 is the joint between the sacrum 52 and each of the ilia 60, 62.

Advantages and improvements of the present medial to lateral posterior SIJ fusion technique are as follows. Since S2AI screws have a medial to lateral trajectory and cross the SIJ, aligning the fusion implant with the S2AI screw allows a surgeon to place a fusion implant with minimal to no additional exposure and minimal time or steps added to a surgery. Additionally, being able to reference the S2AI screw during implantation of a SIJ fusion implant may aid in placement, as opposed to having no reference implants in a primary SIJ fusion. Further, the fusion implant is not connected to a rod construct.

One embodiment of a fusion implant 210 ("implant 210") suitable for use in the present method is shown in FIG. 2 and includes an elongate body 212 having at least one and preferably, multiple threads 214. The body 212 has a proximal, or head, end 216 and a distal, or insertion, end 218. The distal end 218 has a minor diameter D1. A cannulation 220 extends through the body 212 between the proximal end 216 and the distal end 218. The proximal end of the body 212 can have internal threads (not shown) to threadingly receive a bone funnel (not shown) to allow graft to be injected into the cannulation 220 after insertion of the implant 210.

The body 212 has a diameter between the proximal end 216 and the distal end 218 of between about 7.5 mm and about 12 mm. At least one graft slot 222 extends through the body 212. In an exemplary embodiment, the graft slot 222 extends generally parallel to the cannula 220.

Alternatively, as shown in FIG. 3, an implant 310, similar to implant 210 described above and having a proximal end 316 and a distal end 318 can include a washer 317 at the proximal end 316. The description below relating to implant 210 is also applicable to implant 310.

Figure 4:
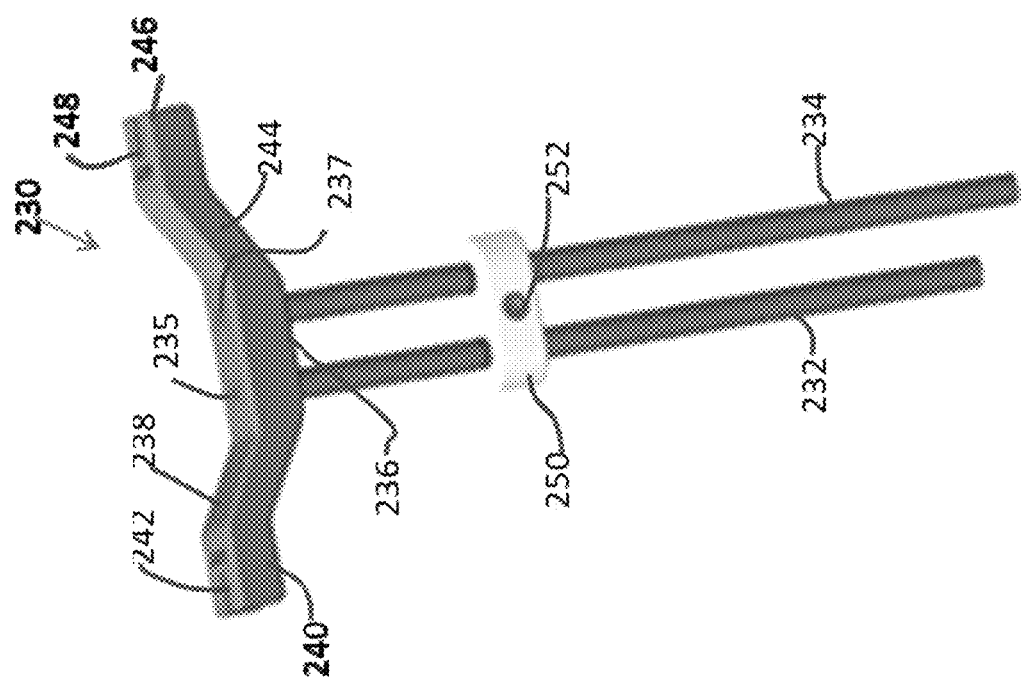
FIG. 4 is a perspective view of an aiming guide according to an exemplary embodiment.

The method may utilize the aiming guide 230 shown, for example, in FIG. 4, to assist in implanting the implant 210 so that the implant 210 is implanted generally parallel to a medial to lateral S2 alar iliac ("S2AI") screw 72 (shown in FIG. 4). The aiming guide 230 includes a cannulated first leg 232 and a cannulated second leg 234 that extends parallel to the first leg 232 of the aiming guide 230. In an exemplary embodiment, the second leg 234 is slightly longer than the first leg 232. The legs 232, 234 are spaced sufficiently far from each other such that enough space is provided between the implant 210 and the S2AI screw 72 at the distal ends of the legs 232, 243 such that the implant 210 and the S2AI screw 72 do not hit or otherwise interfere with each other. The legs 232, 234 have a generally tubular cross section, although those skilled in the art will recognize that the legs 232, 234 can have other cross sectional shapes.

A handle 236 extends generally perpendicularly to the first leg 232 and the second leg 234. The handle 236 includes a first through-opening 235 that is in fluid communication with the cannulated first leg 232 and a second through-opening 237 that is in fluid communication with the cannulated second leg 234. The handle 236 also includes a first wing 238 that extends upwardly and away from the first leg 232. A free end 240 of the first wing 238 includes an open slot 242.

Similarly, the handle 236 also includes a second wing 244 that extends upwardly and away from the second leg 234. A free end 246 of the second wing 244 includes an open slot 248. The open slots 242, 248, are sized and configured to each accept an insertion instrument 80 (shown in FIG. 4), such as, for example, a port mount handle (Globus Medical Part No. 639.413), an articulating arm assembly (Globus Medical Part No. 632.750 or 6133.0780, or other suitable instrument, to allow the implanting surgeon to better stabilize the aiming guide 230 during implantation of the implant 210 into the joint 50.

Referring back to FIG. 4, a stabilizer cuff 250 connects the first leg 232 to the second leg 234. The stabilizer cuff 250 is slidable along the length of legs 232, 234 so that the stabilizer cuff 250 can be pressed against the iliac wing 64 of the ilium 60 that is presently not being fused to the sacrum 52 (shown in FIG. 5). A screw 252 extends into the stabilizer cuff 250 between the legs 232, 234. The screw 252 can be tightened to releasably secure the stabilizer cuff 250 to the legs 232, 234 at a desired location to prevent the translation of the stabilizer cuff 250 along the legs 232, 234.

Figure 6:
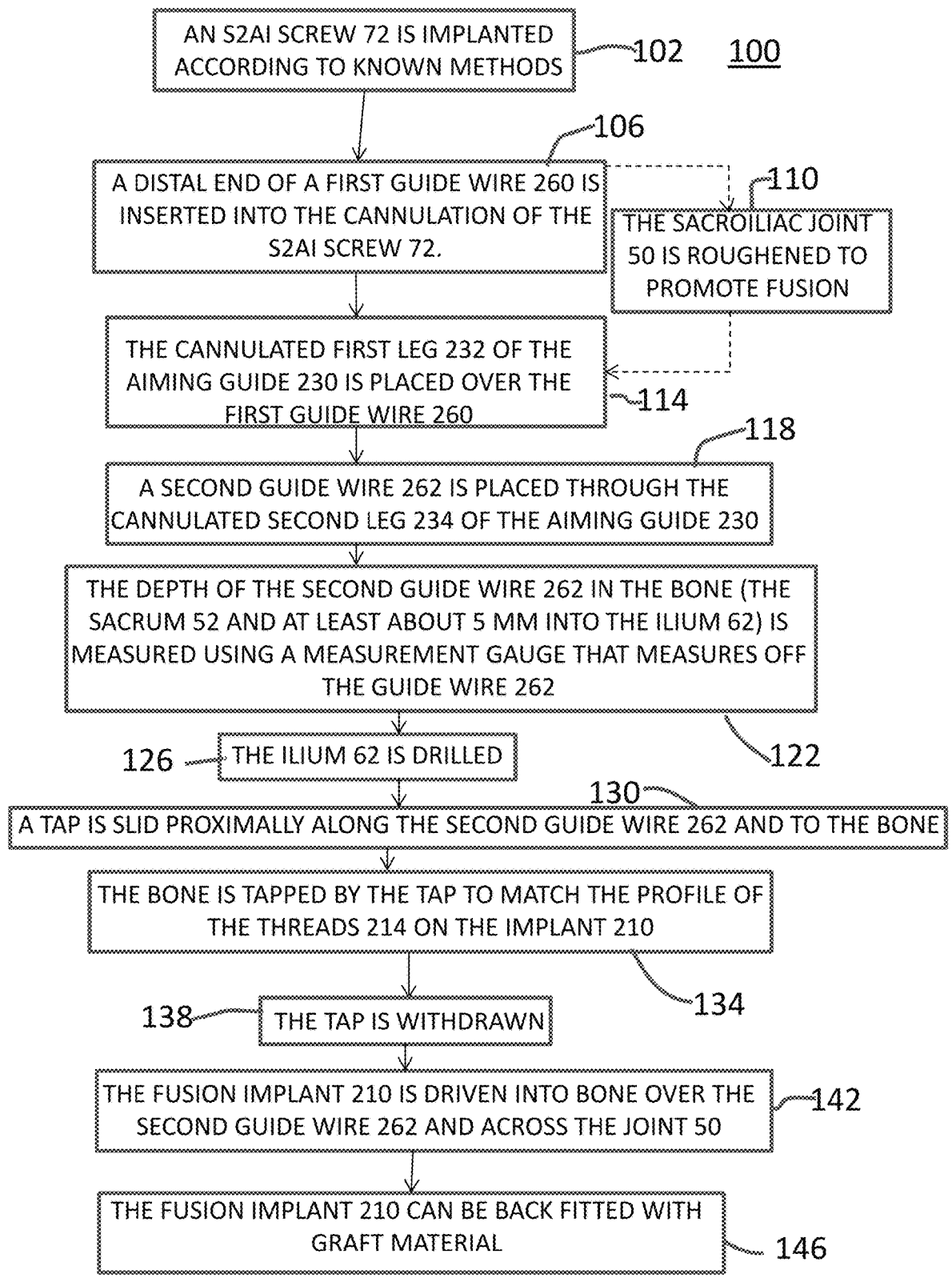
FIG. 6 is a flowchart of an exemplary method of implanting the implant of FIG. 2 or FIG. 3.

An exemplary method of fusing a sacroiliac joint is illustrated in the Figures and outlined in the flowchart 100 of FIG. 6. In step 102, the S2AI screw 72 is implanted according to known methods. The S2AI screw 72 has a proximal end 74 and a distal end 76 and is cannulated, with a cannulation extending at least from the proximal end 74 and toward the distal end 76. In an exemplary embodiment, the S2AI screw 72 is implanted into the sacrum 52 about 1 mm caudal and about 1 mm lateral to the caudal border of the first sacral foramen S1 (shown in FIG. 1) and into the ilium 62

In step 106, a distal end of a first guide wire 260 is inserted into the proximal end 74 and into the cannulation of the S2AI screw 72. In an exemplary embodiment, the first guide wire 260 can be a K-wire.

Optionally, in step 110, the sacroiliac joint 50 can be roughened to promote fusion. An instrument with a rough surface (not shown) can be used to enhance fusion across the sacroiliac joint. In an open procedure, the posterior portion of the sacroiliac joint 50 is exposed, allowing for widespread and open decortication of the sacroiliac joint 50. This step is typically unavailable during a minimally invasive approach or in a lateral to medial approach.

Next, in step 114, the cannulated first leg 232 of the aiming guide 230 is placed over the first guide wire 260. As shown in FIG. 5, the insertion instrument 80 is attached to the aiming guide 230 to allow the clinician to manipulate the aiming guide 230. In step 118, a second guide wire 262 is inserted into the second through-opening 237 and placed through the cannulated second leg 234 of the aiming guide 230. In an exemplary embodiment, the second guide wire 262 can be a K-wire.

The second guide wire 262 is used to guide the implant 210 across the joint 50 at a 45 degree medial to lateral angle. The second guide wire 262 can be driven into the bone by a mallet or a wire driver (not shown). The "bone" can be just the sacrum 52 or the sacrum 52 and the ilium 62 across the SIJ 50. In step 118, after the second guide wire 262 is placed, the aiming guide 230 is removed, leaving the guide wire 262 in place.

Next, in step 122, the depth of the second guide wire 262 in the bone (the sacrum 52 and at least 5 mm into the ilium 62 is measured using a measurement gauge (not shown) that measures off the guide wire 262, according to known methods. Then, in step 126, the ilium 62 is drilled, using a cannulated drill having a diameter generally equal to the minor diameter (diameter of body 212) D1 of the implant 210. The cannulation of the drill is sized to allow the drill to fit over the second guide wire 262. In an exemplary embodiment, the bone is drilled just across the cortical walls of the joint 50. After drilling the bone, the drill is withdrawn proximally from the second guide wire 262.

Next, in step 130, a tap, cannulated to be able to slide over the guide wire 262, is slid distally along the second guide wire 262 and to the bone. In step 134, the bone is tapped by the tap to match the profile of the threads 214 on the implant 210. In an exemplary embodiment, the clinician can tap just past the cortical wall of the sacrum 50 or, alternatively, the clinician can tap the entire length of screw 210. After tapping the bone, in step 138, the tap is withdrawn proximally from the second guide wire 262.

In step 142, as shown in FIG. 7, the fusion implant 210 is driven into bone over the second guide wire 262 and across the joint 50. The fusion implant 210 lies below a construct rod 70 due to the lack of a large screw tulip on the fusion implant 210. The profile of the fusion implant 210 above the sacrum 52 is less than that of the profile of the S2AI screw 72. The fusion implant 210 is also tucked below the iliac wing 66 for minimal prominence into soft tissue.

Next, in step 146, the fusion implant 210 can be back filled with graft material. The proximal end of the body 212 of the implant 210 includes threads (not shown) for a bone funnel and pusher (not shown). The implant 210 includes several slots 222 (one slot 222 shown in FIG. 2) intended to be filled with bone graft for fusion. A portion of slot 222 extends across the entire length of the implant 210 to ensure crossing of the SIJ 50. The implant 210 can be headless to rest on the cortical wall of the sacrum 52 or to recess into the sacrum 52.

Figure 9:
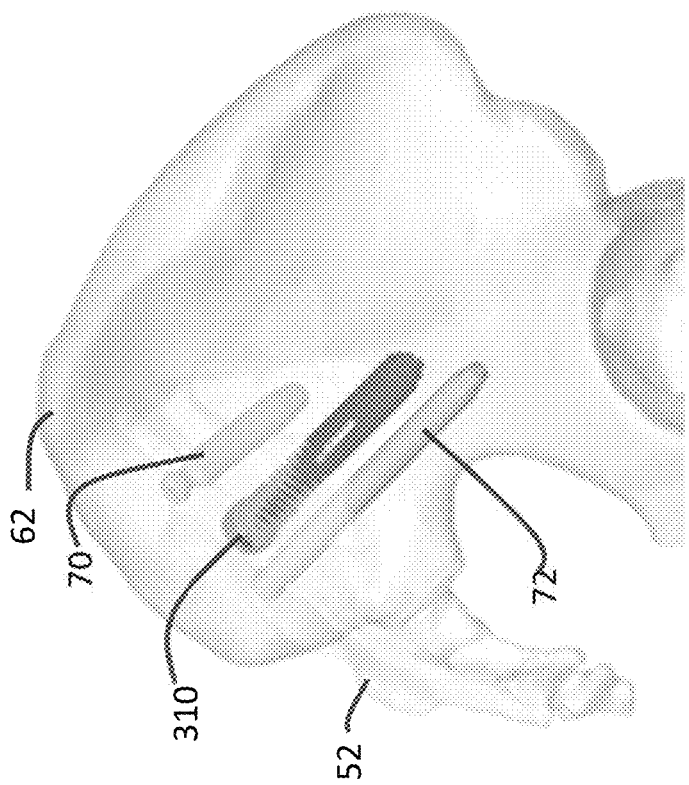
FIG. 9 is a lateral view of the implant of FIG. 3 implanted in the sacroiliac joint.
Figure 8:
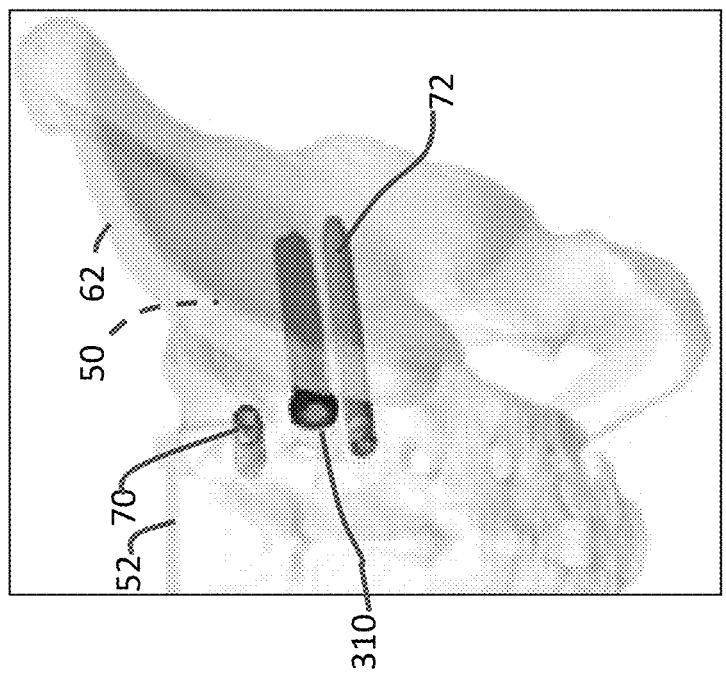
FIG. 8 is a partial posterior view of the implant of FIG. 3 implanted in the sacroiliac joint.

FIGS. 8 and 9 show a posterior view and a lateral view, respectively, of the implant 310 after implantation to fuse the SIJ joint 50.

The present technique can then be applied on the contralateral side of the construct. Because the implants 210, 310 are cannulated, the implants 210, 310 can be inserted in a minimally invasive fashion. Optionally, the implants 210, 310 can be coated, roughened, treated, or 3D printed to improve osseointegration. The implants 210, 310 can be alternatively driven by image guided methods or robotic platforms. Further, the present implant approach is applicable to open or percutaneous primary SIJ fusion.

It will be further understood that various changes in the details, materials, and arrangements of the parts which have been described and illustrated in order to explain the nature of this device may be made by those skilled in the art without departing from the scope of the device as expressed in the following claims.

What is claimed is:

1. A method of fusing a sacroiliac joint with a fusion implant comprising:
   inserting a first cannulated screw into a sacrum in a medial to lateral direction such that the first cannulated screw is inserted into the sacrum, through the sacroiliac joint and then through the ilium;
   with an aiming guide having first and second cannulated legs, placing the first leg over the first cannulated screw;
   inserting a second leg guide wire through the second leg of the aiming guide and into bone;
   while maintaining the position of the second leg guide wire, removing the aiming guide; and
   inserting a fusion implant over the second guide wire and into the sacroiliac joint in a medial to lateral direction.

2. The method according to claim 1, prior to the step of placing the first leg over the first cannulated screw, further comprising inserting a first leg guide wire into the first cannulated screw, wherein the step of placing the first leg includes placing the first leg over the first leg guide wire.

3. The method according to claim 1, prior to the step of inserting a fusion implant, further comprising:
   measuring a depth of the second leg guide wire in the bone; and
   drilling and tapping the bone over the inserted second leg guidewire.

4. The method according to claim 1, after the step of inserting a first cannulated screw into a sacrum, further comprising roughening the sacroiliac joint.

5. The method according to claim 1, wherein the step of inserting a fusion implant comprises inserting the fusion implant in a medial-to-lateral S2 alar iliac trajectory.

6. The method according to claim 1, wherein the step of inserting a fusion implant comprises inserting the fusion implant having at least one graft slot extending therethrough.

7. The method according to claim 6, after the step of inserting a fusion implant, further comprising back-filling the fusion implant with a graft material.

8. The method according to claim 7, wherein the step of back-filling comprises the step of attaching a bone funnel to the implant.

9. The method according to claim 8, wherein the step of back-filling further comprises the step of using a pusher to back-fill the graft material into the implant.

10. The method according to claim 1, wherein the step of inserting a fusion implant comprises inserting the fusion implant at an angle within 10 degrees of a trajectory of the first cannulated screw.

11. The method according to claim 1, wherein the step of inserting a fusion implant comprises inserting the fusion implant above the first cannulated screw.

12. The method according to claim 1, wherein the step of inserting a fusion implant comprises inserting the fusion implant below the first cannulated screw.

13. The method according to claim 1, wherein the step of inserting a first cannulated screw comprises inserting the first cannulated screw having a diameter between about 7.5 mm and about 12 mm.

14. A method of fusing a sacroiliac joint comprising:
(a) providing an aiming guide having:
  a first cannulated leg;
  a second cannulated leg extending generally parallel to the first cannulated leg; and
  a handle connected to the first and second legs;
(b) inserting a first cannulated screw into a sacrum from a medial to lateral direction;
(c) inserting a first guide wire into the first cannulated screw;
(d) inserting the first leg of an aiming guide over the first guide wire;
(e) inserting a second guide wire through the second leg of the aiming guide and into bone;
(f) removing the aiming guide while maintaining the position of the second guide wire;
(g) drilling and tapping the bone over the second guide wire; and
(h) inserting a fusion implant over the second guide wire and into the sacroiliac joint in a medial to lateral direction.

15. The method according to claim 14, wherein step (a) comprises providing a first wing and a second wing on the handle for attaching to an insertion instrument.

16. The method according to claim 14, wherein:
step (a) comprises providing a first wing and a second wing on the handle for attaching to an insertion instrument; and
attaching an insertion instrument to the first or second wing.

17. The method according to claim 16, wherein the first wing includes a first open slot and the second wing includes a second open slot and wherein the step of attaching includes attaching the insertion instrument through either the first open slot or the second open slot.

18. The method according to claim 14, wherein step (a) further comprises providing a cuff slidingly disposed along the first leg and the second leg.

19. The method according to claim 18, wherein the cuff is releasably securable to the first leg and to the second leg.

20. A method of fusing a sacroiliac joint together comprising the steps of:
(a) inserting a first screw into a sacrum from a medial to lateral direction;
(b) inserting a first guide wire into the first screw;
(c) inserting a second guide wire to bone;
(d) inserting a drill over the second guide wire;
(e) drilling the bone with the inserted drill; and
(f) inserting a fusion implant over the second guide wire and into the sacroiliac joint in a medial to lateral direction.

* * * * *